United States Patent
Young et al.

(10) Patent No.: US 9,534,251 B2
(45) Date of Patent: Jan. 3, 2017

(54) IN VITRO RECOMBINATION METHOD

(75) Inventors: Lei Young, Gaithersburg, MD (US);
Hamilton O. Smith, San Diego, CA (US); Daniel Glenn Gibson, Crofton, MD (US)

(73) Assignee: Synthetic Genomics, Inc., La Jolla, CA (US)

( * ) Notice: Subject to any disclaimer, the term of this patent is extended or adjusted under 35 U.S.C. 154(b) by 308 days.

(21) Appl. No.: 12/750,571

(22) Filed: Mar. 30, 2010

(65) Prior Publication Data

US 2010/0184187 A1    Jul. 22, 2010

Related U.S. Application Data

(62) Division of application No. 11/502,746, filed on Aug. 11, 2006, now Pat. No. 7,723,077.

(60) Provisional application No. 60/707,160, filed on Aug. 11, 2005.

(51) Int. Cl.
| | |
|---|---|
| C12N 9/00 | (2006.01) |
| C12Q 1/68 | (2006.01) |
| C12N 15/66 | (2006.01) |
| C12N 15/10 | (2006.01) |

(Continued)

(52) U.S. Cl.
CPC ............ *C12Q 1/6862* (2013.01); *C12N 15/10* (2013.01); *C12N 15/64* (2013.01); *C12N 15/66* (2013.01); *C12P 19/34* (2013.01)

(58) Field of Classification Search
None
See application file for complete search history.

(56) References Cited

U.S. PATENT DOCUMENTS

| | | |
|---|---|---|
| 4,582,802 A | 4/1986 | Zimmerman et al. |
| 5,075,227 A | 12/1991 | Hagen |
| 5,534,407 A | 7/1996 | Tabor et al. |

(Continued)

FOREIGN PATENT DOCUMENTS

| | | |
|---|---|---|
| EP | 1 403 379 A1 | 3/2004 |
| EP | 1 482 036 A2 | 12/2004 |

(Continued)

OTHER PUBLICATIONS

Anand R., "Yeast artificial chromosomes (YACs) and the analysis of complex genomes", *Trends in Biotechnol*, (1992) 10:35-40.

(Continued)

*Primary Examiner* — Samuel Woolwine
(74) *Attorney, Agent, or Firm* — DLA Piper LLP (US)

(57) ABSTRACT

The present invention relates, e.g., to in vitro method, using isolated protein reagents, for joining two double stranded (ds) DNA molecules of interest, wherein the distal region of the first DNA molecule and the proximal region of the second DNA molecule share a region of sequence identity, comprising contacting the two DNA molecules in a reaction mixture with (a) a non-processive 5' exonuclease; (b) a single stranded DNA binding protein (SSB) which accelerates nucleic acid annealing; (c) a non strand-displacing DNA polymerase; and (d) a ligase, under conditions effective to join the two DNA molecules to form an intact double stranded DNA molecule, in which a single copy of the region of sequence identity is retained. The method allows the joining of a number of DNA fragments, in a predetermined order and orientation, without the use of restriction enzymes.

9 Claims, 6 Drawing Sheets

(51) Int. Cl.
C12N 15/64 (2006.01)
C12P 19/34 (2006.01)

(56) References Cited

U.S. PATENT DOCUMENTS

| | | | |
|---|---|---|---|
| 5,616,478 | A | 4/1997 | Chetverin et al. |
| 6,008,031 | A | 12/1999 | Modrich et al. |
| 6,150,111 | A | 11/2000 | HungTseng |
| 6,379,964 | B1 | 4/2002 | del Cardayre et al. |
| 6,521,427 | B1 | 2/2003 | Evans |
| 6,576,453 | B2 | 6/2003 | Barany et al. |
| 6,582,914 | B1 | 6/2003 | Caldwell et al. |
| 6,617,137 | B2 | 9/2003 | Dean et al. |
| 6,991,922 | B2 | 1/2006 | Dupret et al. |
| 2001/0044142 | A1 | 11/2001 | Brown et al. |
| 2002/0052029 | A1 | 5/2002 | Quanz et al. |
| 2003/0032033 | A1 | 2/2003 | Anglin et al. |
| 2003/0119150 | A1 | 6/2003 | Ankenbauer et al. |
| 2003/0165946 | A1 | 9/2003 | Evans |
| 2003/0224481 | A1 | 12/2003 | Elledge et al. |
| 2004/0023207 | A1* | 2/2004 | Polansky ............ 435/5 |
| 2004/0096929 | A1* | 5/2004 | Kawasaki et al. ......... 435/25 |
| 2005/0112631 | A1 | 5/2005 | Piepenburg et al. |
| 2005/0191623 | A1 | 9/2005 | Jarrell et al. |
| 2005/0272074 | A1 | 12/2005 | Arezi |
| 2007/0004041 | A1 | 1/2007 | Church et al. |
| 2007/0037196 | A1 | 2/2007 | Gibson et al. |
| 2007/0037197 | A1 | 2/2007 | Young et al. |
| 2007/0128649 | A1 | 6/2007 | Young |
| 2007/0264688 | A1 | 11/2007 | Venter et al. |

FOREIGN PATENT DOCUMENTS

| | | |
|---|---|---|
| WO | WO 94/09127 A2 | 4/1994 |
| WO | WO 98/38297 A1 | 9/1998 |
| WO | WO 00/15779 A2 | 3/2000 |
| WO | WO 01/66775 A2 | 9/2001 |
| WO | WO 2004/096288 A2 | 11/2004 |
| WO | WO 2005/028629 A2 | 3/2005 |
| WO | WO 2007/021944 A2 | 2/2007 |
| WO | WO 2007/032837 A2 | 3/2007 |
| WO | WO/2007/124065 A1 | 11/2007 |

OTHER PUBLICATIONS

Andersson et al., "A "double adaptor" method for improved shotgun library construction", *Anal. Biochem.*, 1996;236(1):107-13.

Bambot and Russell, "Efficient total gene synthesis of 1.35-kb hybrid alpha-lytic protease gene using the polymerase chain reaction", *PCR Methods, Appl.* Feb. 1993;2(3):266-71.

Blight et al. "Efficient initiation of HCV RNA replication in cell culture", *Science*, Dec. 8, 2000;290(5498):1972-4.

Burke et al., "Cloning of large segments of exogenous DNA into yeast by means of artificial chromosome vectors", *Science*, May 15, 1987;236(4803):806-12.

Cello et al, "Chemical synthesis of poliovirus cDNA: generation of infectious virus in the absence of natural template", *Science*, Aug. 9, 2002;297(5583):1016-8.

Chang et al., "Structure and function of the *Escherichia coli* RecE protein, a member of the RecB nuclease domain family", *The Journal of Biological Chemistry*, 276(49):46004-46010 (2001).

Chebotareva et al., "Biochemical effects of molecular crowding", *Biochemistry (Mosc)*, Nov. 2004;69(11):1239-51.

Coljee et al., "Seamless gene engineering using RNA- and DNA-overhang cloning", *Nat. Biotechnol.*, Jul. 2000;18(7):789-91.

Daly and Minton, "An alternative pathway of recombination of chromosomal fragments precedes recA-dependent recombination in the radioresistant bacterium *Deinococcus radiodurans*", *J. Bacterial.*, Aug. 1996;178(15):4461-71.

Dean et al., "Rapid amplification of plasmid and phage DNA using Phi 29 DNA polymerase and multiply-primed rolling circle amplification", *Genome Res.*, Jun. 2001;11(6):1095-9.

Dekker et al., "Joining of long double-stranded RNA molecules through controlled overhangs", *Nucleic Acids Res.*, Oct. 8, 2004;32(18):e140.

Detter et al., "Isothermal strand-displacement amplification applications for high-throughput genomics", *Genomics*, Dec. 2002;80(6):691-8.

Ebersole et al., "Rapid generation of long synthetic tandem repeats and its application for analysis in human artificial chromosome formation", *Nucleic Acids Res.*, Sep. 1, 2005;33(15):e130.

Endo and Sawasaki, "High-throughput, genome-scale protein production method based on the wheat germ cell-free expression system", *Biotechnol. Adv.*, Nov. 2003;21(8):695-713.

European Search Report for EP 06751837.3, mailed Apr. 29, 2008, 10 pages.

Final Office Action for U.S. Appl. No. 11/502,624, mailed Feb. 21, 2008.

Final Rejection for U.S. Appl. No. 11/502,624, mailed Aug. 11, 2008.

Fire and SQ, "Rolling replication of short DNA circles", *Proc. Natl. Acad. Sci. U.S.A.*, May 9, 1995;92(10):4641-5.

Gibson et al., "Complete chemical synthesis, assembly, and cloning of a Mycoplasma genitalium genome", *Science*, Feb. 29, 2008;319(5867):1215-20.

Glass et al., "Essential genes of a minimal bacterium", *Proc. Natl. Acad. Sci. U.S.A.*, Jan. 10, 2006;103(2):425-30.

Hinkle and Richardson, "Bacteriophage T7 deoxyribonucleic acid replication in vitro", *J. Biol. Chem.*, 249(9):2974-2980 ()1974).

Hutchison et al., "Cell-free cloning using phi29 DNA polymerase", *Proc. Natl. Acad. Sci. U.S.A.*, Nov. 29, 2005;102(48):17332-6.

International Search Report and Written Opinion for PCT/US08/79109, mailed Jun. 24, 2009, 9 pages.

International Search Report and Written Opinion for PCT/US09/34153, mailed May 11, 200912 pages. International Search Report and Written Opinion for PCT/US2006/031214, mailed Apr. 3, 2007.

Itaya et al., "Combining two genomes in one cell: stable cloning of the Synechocystis PCC6803 genome in the Bacillus subtilis 168 genome", *Proc. Natl. Acad. Sci. U.S.A.*, Nov. 1, 2005;102(44):15971-6.

Kaluz et al., "Directional cloning of PCR products using exonuclease III", *Nucleic Acids Res.*, Aug. 25, 1992;20(16):4369-70.

Kuijper et al., "Functional cloning vectors for use in directional cDNA cloning using cohesive ends produced with T4 DNA polymerase", *Gene*, Mar. 15, 1992;112(2):147-55.

Lai and Masker, "In vitro repair of gaps in bacteriophage T7 DNA", *J. Bacteriol.*, 180(23):6193-6202 (1998).

Lai and Masker, "Visualization of repair of double-strand breaks in the bacteriophage T7 genome without normal DNA replication", *J. Bacteriol.*, Jan. 2000;181(2):327-36.

Lee and Sadowski, "In vitro recombination of bacteriophage T7 DNA detected by a direct physical assay", *J. Virol.*, Dec. 1983;48(3):647-53.

Li and Elledge, "Harnessing homologous recombination in vitro to generate recombinant DNA via SLIC", *Nat. Methods*, Mar. 2007;4(3):251-6.

Li and Evans, "Ligation independent cloning irrespective of restriction site compatibility", *Nucleic Acids Res.*, Oct. 15, 1997;25(20):4165-6.

Liu et al., "Rolling Circle DNA Synthesis: Small Circular Oligonucleotides as Efficient Templates for DNA Polymerases", *J. Am. Chem. Soc.*, Feb. 21, 1996;118(7):1587-1594.

Meixia Zhou et al., "An improved ligase-free method for directional subcloning of PCR amplified DNA," Nucleic Acids Research, 1995, pp. 1089-1090, vol. 23, No. 6, 1995 Oxforford University Press.

Meyer et al., "Combinatorial recombination of gene fragments to construct a library of chimeras", *Curr. Protoc. Protein Sci.*, Jun. 2006;Chapter 26:Unit 26.2.

Mitra and Church, "In situ localized amplification and contact replication of many individual DNA molecules"*Nucleic Acids Res.*, Dec. 15, 1999;27(24):e34.

Muyrers et al, "Techniques: Recombinogenic engineering—new options for cloning and manipulating DNA", *Trends in Biochemical Sciences*, 26(5):325-331 (2001).

(56) References Cited

OTHER PUBLICATIONS

Muyrers et al., "RecE/RecT and Redalpha/Redbeta initiate double-stranded break repair by specifically interacting with their respective partners", *Genes Dev.*, Aug. 1, 2000;14(15):1971-82.
Nakano et al., "Single-molecule PCR using water-in-oil emulsion", *J. Biotechnol.*, Apr. 24, 2003;102(2):117-24.
Nelson et al., "TempliPhi, phi29 DNA polymerase based rolling circle amplification of templates for DNA sequencing", *Biotechniques*, Jun. 2002;Suppl:44-7.
New England Biolabs Catalog (1993/94) p. 69.
Non-Final Office Action for U.S. Appl. No. 11/502,624, mailed Jul. 25, 2007.
Non-Final Office Action for U.S. Appl. No. 11/502,624, mailed Jul. 6, 2009.
Non-Final Office Action for U.S. Appl. No. 11/919,515, mailed Aug. 19, 2009.
Noskov et al., "Defining the minimal length of sequence homology required for selective gene isolation by TAR cloning", Nucleic Acids Res. Mar. 15, 2001;29(6):E32.
Notice of Appeal for U.S. Appl. No. 11/502,624, filed Feb. 11, 2009.
Office Action for EP 06836102.1, mailed May 20, 2009.
Pfeiffer et al., "Mechanisms of overlap formation in nonhomologous DNA end joining", *Mol. Cell. Biol.*, Feb. 1994;14(2):888-95.
Raymond et a., "General method for plasmid construction using homologous recombination", *Biotechniques*, Jan. 1999;26(1):134-8, 140-1.
Raymond et al., "Linker-mediated recombinational subcloning of large DNA fragments using yeast", *Genome Res.*, Jan. 2002;12(1):190-7.
Rector et al., "A sequence-independent strategy for detection and cloning of circular DNA virus genomes by using multiply primed rolling-circle amplification", *J. Virol.* May 2004;78(10):4993-8.
Request for Continued Examination for U.S. Appl. No. 11/502,624, filed Jul. 18, 2008.
Request for Continued Examination for U.S. Appl. No. 11/502,624, filed Jun. 11, 2009.
Response to Office Action for U.S. Appl. No. 11/502,624, filed Dec. 26, 2007.
Response to Restriction Requirement for U.S. Appl. No. 11/502,624, filed Jun. 13, 2007.
Restriction Requirement for U.S. Appl. No. 11/502,624, mailed May 15, 2007.
Rezende et al., "Essential amino acid residues in the single-stranded DNA-binding protein of bacteriophage T7. Identification of the dimer interface", *J. Biol. Chem.*, Dec. 27, 2002;277(52):50643-53.
Rolf Jessberger et al., "A Mammalian Protein Complex That Repairs Double-strand Breaks and Deletions by Recombination," *The Journal of Biological Chemistry*, 1993, pp. 15070-15079, vol. 268, No. 20, Issue of Jul. 15, 1993 The American Society of Biochemistry and Molecular Biology, Inc.
Rubin et al., "Convergent DNA synthesis: a non-enzymatic dimerization approach to circular oligodeoxynucleotides", *Nucleic Acids Res.*, Sep. 11, 1995;23(17):3547-53.
Smith et al., "Generating a synthetic genome by whole genome assembly: phiX174 bacteriophage from synthetic oligonucleotides", *Proc. Natl. Acad. Sci. U.S.A.*, Dec. 23, 2003;100(26):15440-5.
Stemmer et al., "Single-step assembly of a gene and entire plasmid from large numbers of oligodeoxyribonucleotides", *Gene*, Oct. 16, 1995;164(1):49-53.
Stoker A.W., "Cloning of PCR products after defined cohesive termini are created with T4 DNA polymerase", *Nucleic Acids Res.*, Jul. 25, 1990;18(14):4290.
Subramanian et al., "The enzymatic basis of processivity in lambda exonuclease", *Nucleic Acids Research*, 31(6):1585-1596 (2003).
Tabor S., Exonucleases, *Current Protocols in Molecular Biology* 3.11.1-3.11.4, John Wiley & Sons, Inc. (2000).
Yang et al., "Construction of recombinant DNA by exonuclease recession", *Nucleic Acids Res.*, Apr. 25, 1993;21(8)1889-93.
Ying-Ta Lai et al., "Repair of double-strand breaks by incorporation of a molecule of homologous DNA," *Molecular Microbiology*, 2000, pp. 437-446, vol. 36, No. 2, 2000 Blackwell Science Ltd.
Yu and Masker, "T7 single strand DNA binding protein but not T7 helicase is required for DNA double strand break repair", *J. Bacteriol.*, Mar. 2001;183(6):1862-9.
Yu et al., "Recombineering with overlapping single-stranded DNA oligonucleotides: testing a recombination intermediate", *Proc. Natl. Acad. Sci. U.S.A.*, Jun. 10, 2003;100(12):7207-12.
Zhou and Doetsch, "Effects of abasic sites and DNA single-strand breaks on prokaryotic RNA polymerases", *Proc. Natl. Acad. Sci. U.S.A.* Jul. 15, 1993;90(14):6601-5.

\* cited by examiner

IN VITRO RECOMBINATION METHOD

CROSS-REFERENCE TO RELATED APPLICATIONS

The present application is a division of U.S. patent application Ser. No. 11/502,746 filed Aug. 11, 2006, which claims benefit and priority of U.S. Provisional Patent Application Ser. No. 60/707,160 filed on Aug. 11, 2005 and titled "In Vitro Recombination Method." The contents of these applications are herein incorporated by reference in their entirety.

This invention was made with government support (DOE grant number DE-FG02-02ER63453). The government has certain rights in the invention.

FIELD OF THE INVENTION

This invention relates, e.g., to in vitro methods for joining (recombining) double stranded DNA molecules via a region of homology. In one embodiment, a plurality of DNA molecules are joined into a longer DNA molecule in a predefined order and orientation.

BACKGROUND INFORMATION

Homologous recombination of linear double stranded DNA has long been known to be crucial for the repair of double stranded DNA breaks. In most organisms, the initiation of homologous recombination requires the action of an exodeoxyribonuclease. The single stranded DNA fragment generated can then pair with homologous sequence on other DNA molecules to complete the recombination. Although homologous recombination has been intensely studied, the mechanism involved is still not fully understood. The most efficient homologous recombination system has been discovered in *Deinococcus radiodurans*, which can survive 15,000 Gy of ionizing radiation, while doses below 10 Gy are lethal to almost all other organisms (Daly et al. (1996) *J. of Bacteriology* 178, 4461-4471). However, due to the complexity of the *D. radiodurans* genome, it is extremely difficult to pinpoint the proteins involved in the homologous recombination process.

Homologous recombination has also been demonstrated in the enterobacteria phage T7 system, the efficiency of which can be more than 50% (Lai et al. (1998) *J. of Bacteriology* 180, 6193-6202). T7 phage contain only 56 genes which encode 59 proteins, and therefore would be a more suitable system to isolate proteins involved in homologous recombination. In the T7 genome, genes that are involved in similar functions are normally clustered together. It has been reported that the early genes from gene 1.3 ligase to gene 6 exonuclease may be important in recombination (Lee et al. (1983) *J. of Virology* 48, 647-653; Lai et al. (1998), supra; Lai et al. (2000) *Molecular Microbiology* 36, 437-466; Yu et al. (2001) *J. of Bacteriology* 183, 1862-1869). However, it is not known whether host proteins are also important in this process.

DESCRIPTION OF THE INVENTION

Figure 1:
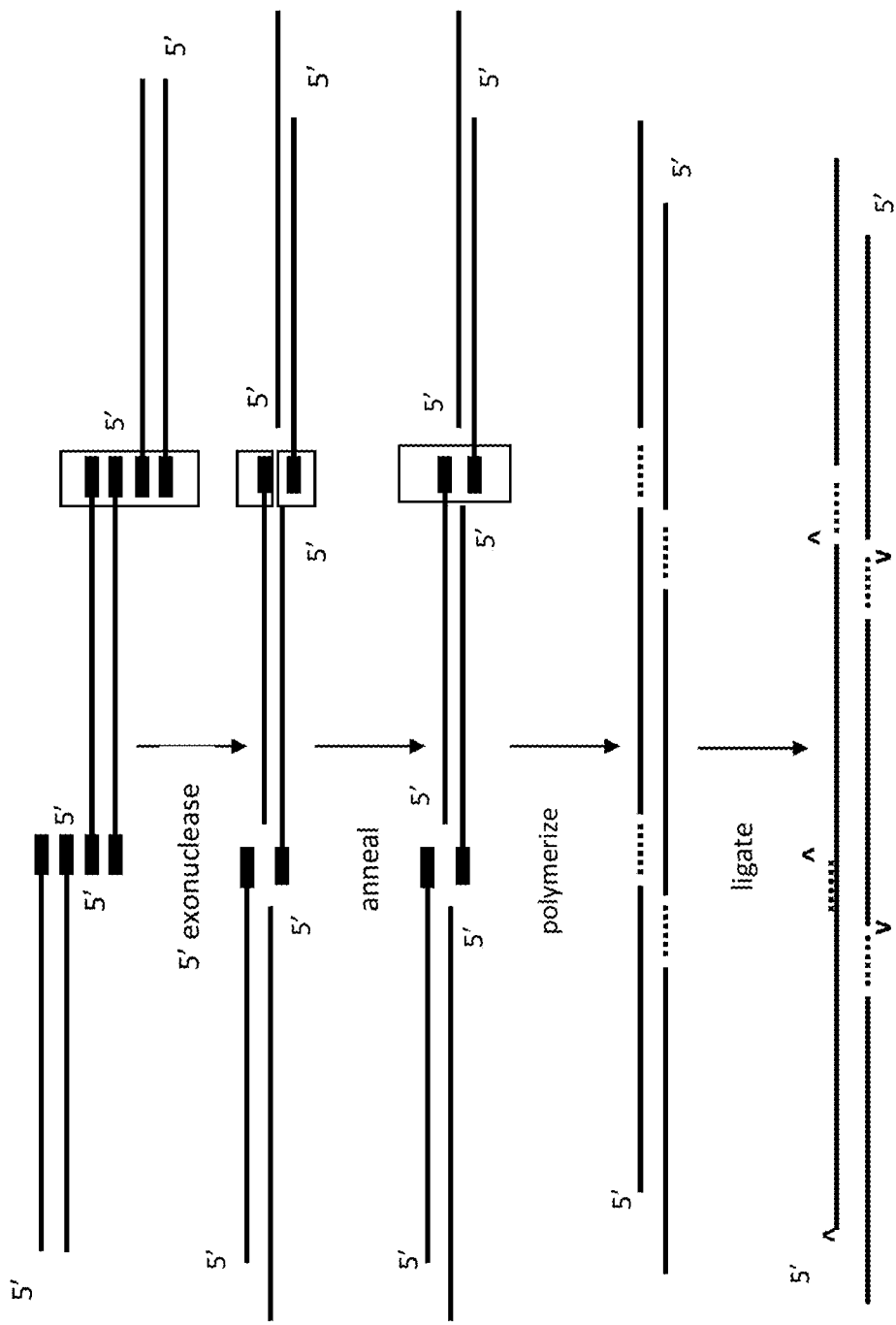
FIG. 1 is a cartoon illustrating a joining reaction of the invention. The joined molecules are shown as linear molecules; however, it is to be understood that the ends of the linear molecule are preferably joined to form a circle, and/or are joined to a linearized vector, to form a circle.

The present inventors have identified four T7 gene products (or substitutes therefor) that are sufficient to constitute an in vitro system for recombining DNAs via a region of homology. The method allows, e.g., for the joining of DNA molecules of interest to one another in a predefined order and orientation, without the use of restriction enzymes.

The present invention relates, e.g., to an in vitro method, using isolated protein reagents (proteins), for joining two double stranded (ds) DNA molecules of interest, wherein the distal region of the first DNA molecule and the proximal region of the second DNA molecule share a region of sequence identity, comprising contacting the two DNA molecules with (a) a non-processive 5' exonuclease;
(b) a single stranded DNA binding protein (SSB) which accelerates nucleic acid annealing;
(c) a non strand-displacing DNA polymerase; and
(d) a ligase, under conditions effective to join the two DNA molecules to form a substantially intact (un-nicked) double stranded DNA molecule in which a single copy of the region of sequence identity is retained. In this method, the 5' exonuclease generates 3' single stranded overhangs in both DNA molecules which comprise the region of sequence identity; the two single stranded overhangs anneal to form a gapped molecule; the DNA polymerase fills in the gaps; and the ligase seals the nicks. The method is illustrated schematically in FIG. 1.

The "joining" of two DNA molecules so that a single copy of the region of sequence identity is retained is sometimes referred to herein as "recombination" of the two DNA molecules. In the method of the invention, the four proteins (a) through (d) are each isolated (e.g., purified); cell extracts are not employed. The four proteins act together in a concerted fashion; the individual enzymatic reactions are not actively terminated (e.g., by an experimenter or investigator) before a subsequent reaction begins. In some embodiments, formation of a double stranded DNA molecule results in the molecule being relatively withdrawn or inert from the reactions. Conditions which are effective for joining the two DNA molecules allow for the net assembly of DNA molecules, rather than the degradation of the DNA molecules by the exonuclease. That is, the gaps formed by digestion by the 5' exonuclease are filled in by the polymerase substantially immediately after they are formed. This is accomplished by contacting the DNA molecules with a substantially lower amount of 5' exonuclease activity than the amount of DNA polymerase activity.

The method can be used to join more than two DNA molecules. To accomplish this, the DNA molecules to be joined are designed such that, for each pair of DNA molecules to be joined, the distal region of one DNA molecule comprises a region of sequence identity with the proximal region of the other DNA molecule. To facilitate the joining of the DNA molecules in a predetermined orientation and order, each set of distal and proximal regions of sequence identity is selected (designed) to be unique (to be different from the regions of sequence identity of the other pairs of DNA molecules). The method allows a number of DNA molecules to be joined with a single operation (e.g. in a single tube). See FIG. 1 for a schematic representation of such predetermined joining.

Advantages of the method of the invention include the ability to perform the joining (recombination) reactions under well-defined conditions, using well-characterized, isolated (e.g. purified) proteins (e.g. enzymes). This allows the joining reactions to be controlled and reproducible. In the method of the invention, the joining process is not subject to competing reactions brought about by other enzymes in the reaction mixture, such as exonucleases and endonucleases which can be present in cell extracts. The method allows one to recombine regions of sequence identity (homologous regions) that are less than about 150 base pairs in length. This is in contrast, e.g., to recombination systems using cell lysates rather than isolated enzymes; in systems using cell lysates, efficient joining does not occur with overlaps of less than about 150 bp. The ability to join DNA molecules in a defined order and orientation allows, for example, for the cloning of a fragment of interest into a linearized vector in a defined orientation; or for the assembly of component DNA portions of a longer sequence of interest (such as the assembly of component parts of a synthetic gene or genome; or the assembly and cloning of sub-fragments of a DNA which are too large to clone using a PCR amplification step). The method allows one to join and/or clone DNA molecules of interest without having to rely on the presence of restriction enzyme recognition sites at the ends of the fragments to be joined. The in vitro procedure also allows one to assemble DNAs that are unstable and thus would be difficult to clone by a method requiring transformation into and replication in a bacterium. If desired, DNAs assembled by a method of the invention can then be amplified in vitro (e.g., by rolling circle amplification or PCR), again without having to passage the DNA through a bacterium.

One aspect of the invention is an in vitro joining method as above, wherein the 5' exonuclease is the phage T7 gene 6 product, RedA of lambda phage, or RecE of Rac prophage; the SSB is the phage T7 gene 2.5 product, the *E. coli* recA protein, RedB of lambda phage, or RecT of Rac prophage; the DNA polymerase is the phage T7 gene 5 product, phage T4 DNA polymerase, or *E. coli* pol I; and/or the ligase is the phage T7 gene 1.3 product, phage T4 DNA ligase, or *E. coli* DNA ligase.

Another aspect of the invention is an in vitro method, using isolated protein reagents, for joining two double stranded (ds) DNA molecules of interest, wherein the distal region of the first DNA molecule and the proximal region of the second DNA molecule share a region of sequence identity, comprising generating 3' single stranded (ss) overhangs at both ends of the DNA molecules; annealing the single stranded overhangs in the presence of a ssDNA binding protein; filling in the gaps formed, and sealing the nicks.

Another aspect of the invention is a kit for the in vitro joining of a plurality of dsDNA molecules comprising, in separate containers, (a) a mixture of the isolated proteins (i) a single stranded DNA binding protein (SSB) which accelerates nucleic acid annealing (e.g., the T7 gene 2.5 product, the *E. coli* recA protein, RedB of lambda phage, or Rec T of Rac prophage);

(ii) a non strand-displacing DNA polymerase (e.g. the phage T7 gene 5 product, phage T4 DNA polymerase, or *E. coli* pol 1); and (iii) a DNA ligase (e.g., the phage T7 gene 1.3 product, phage T4 DNA ligase, or *E. coli* DNA ligase), wherein the ratios of activities of (i), (ii) and (iii) are effective, when in the presence of a non-processive 5' exonuclease, to achieve in vitro joining of the dsDNA molecules, and (b) an isolated 5' exonuclease (e.g. the phage T7 gene 6 product, RedA of lambda phage, or RecE of Rac prophage).

Another aspect of the invention is a composition comprising (a) an isolated 5' exonuclease (e.g. the phage T7 gene 6 product, RedA of lambda phage, or RecE of Rac prophage);

(b) a single stranded DNA binding protein (SSB) which accelerates nucleic acid annealing (e.g., the T7 gene 2.5 product, the *E. coli* recA protein, RedB of lambda phage, or Rec T of Rac prophage);

(c) a non strand-displacing DNA polymerase (e.g. the phage T7 gene 5' product, phage T4 DNA polymerase, or *E. coli* pol I); and (d) a DNA ligase (e.g, the phage T7 gene 1.3 product, phage T4 DNA ligase, or *E. coli* DNA ligase).

Such a composition can be present, for example, in a reaction mixture in which a plurality of DNA molecules are being joined by a method of the invention.

As used herein, the singular forms "a," "an," and "the" include plural referents unless the context clearly dictates otherwise. For example, "an" isolated exonuclease, as used above, includes two or more exonuclease molecules, which can be the same or different.

The term, an "isolated" protein, as used herein, means that the protein is removed from its original environment (e.g., the natural environment if it is naturally occurring), and isolated or separated from at least one other component with which it is naturally associated. For example, a naturally-occurring protein present in its natural living host (e.g. a bacteriophage protein present in a bacterium that has been infected with the phage) is not isolated, but the same protein, separated from some or all of the coexisting materials in the natural system, is isolated. Such proteins can be part of a composition or reaction mixture, and still be isolated in that such composition or reaction mixture is not part of its natural environment. The term "an isolated protein," as used herein, can include 1, 2, 3, 4 or more copies of the protein, i.e., the protein can be in the form of a monomer, or it can be in the form of a multimer, such as dieter, trimer, tetramer or the like, depending on the particular protein under consideration. In some embodiments, the protein is purified. Methods for purifying the proteins of the invention are conventional. In some embodiments, the protein is substantially purified or is purified to homogeneity. By "substantially purified" is meant that the protein is separated and is essentially free from other proteins, i.e., the protein is the primary and active constituent. The purified protein can then be contacted with the DNAs to be joined, where it then acts in concert with other proteins to achieve the joining. The proteins can be contacted with (combined with) the DNAs in any order; for example, the proteins can be added to a reaction mixture comprising the DNAs, or the DNAs can be added to a reaction mixture comprising the proteins. Proteins used in the methods of the invention can be in the form of "active fragments," rather than the full-length proteins, provided that the fragments retain the activities (enzymatic activities or binding activities) required to achieve the joining. One of skill in the art will recognize how to generate such active fragments.

Any non-processive 5'→3' double strand specific exodeoxyribonuclease may be used in the methods of the invention. The terms "5' exonuclease" or "exonuclease" are sometimes used herein to refer to a 5'→3' exodeoxyribonuclease. A "non-processive" exonuclease, as used herein, is an exonuclease that degrades a limited number (e.g., only a few) nucleotides during each DNA binding event. Among other properties which are desirable for the 5' exonuclease are that it lacks 3' exonuclease activity, it is double strand DNA specific, it generates 5' phosphate ends, and it initiates degradation from both 5'-phosphorylated and unphosphorylated ends. Suitable 5' exonucleases will be evident to the skilled worker. Among the preferred 5' exonucleases are the phage T7 gene 6 product, RedA of lambda phage (lambda exonuclease), RecE of Rac prophage, or any of a variety of 5'→3' exonucleases that are involved in homologous recombination reactions. Methods for preparing the T7 gene 6 product and optimal reaction conditions for using it are conventional. See, e.g., Kerr et al. (1972) *The Journal of Biological Chemistry* 247, 305-310. Methods for preparing and using the other noted exonucleases are conventional; and many are available from commercial sources, such as USB Corporation, 26111 Miles Road, Cleveland, Ohio 44128, or New England Biolabs, Inc. (NEB), 240 County Road, Ipswich, Mass. 01938-2723.

Without wishing to be bound by any particular mechanism of action, it is suggested that a single stranded DNA binding protein (SSB) used in a method of the invention protects the single stranded overhangs generated by the 5' exonuclease, as well as facilitating the rapid annealing of the homologous single stranded regions. Any SSB which accelerates nucleic acid annealing may be used in a method of the invention. An SSB which "accelerates nucleic acid annealing," as used herein, is an SSB which accelerates nucleic acid binding by a factor of greater than about 500 fold, compared to the binding in the absence of the SSB. See, e.g., U.S. Pat. No. 5,534,407. Among other properties which are desirable for the SSB are that it binds single stranded DNA (ssDNA) more tightly than double stranded DNA (dsDNA), and that it interacts with both the exonuclease and the DNA polymerase. Suitable SSBs will be evident to the skilled worker. Among the preferred SSBs are the T7 gene 2.5 product, the *E. coli* RecA protein, RedB of lambda phage, and RecT of Rac prophage. Methods for preparing the T7 protein and optimal reaction conditions for using it are conventional. See, e.g., Rezende et al. (2002) *Journal of Biological Chemistry* 277, 50643-53 and Yu et al. (2001), supra. Methods for preparing and using the other SSBs are conventional; and many are available commercially, e.g. from USB or NEB, as noted above. In yet a further embodiment, polyethylene glycol ("PEG") may be used to enhance the annealing process.

Any non strand-displacing DNA polymerase may be used in the methods of the invention to fill in the gaps left by the 5' exonuclease digestion. The term "polymerase" is sometimes used herein to refer to a DNA polymerse. A "non strand-displacing DNA polymerase," as used herein, is a DNA polymerase that terminates synthesis of DNA when it encounters DNA strands which lie in its path as it proceeds to copy a dsDNA molecule, or degrades the encountered DNA strands as it proceeds while currently with filling in the gap thus created, thereby generating a "moving nick." Among the other properties which are desirable for the non strand-displacing DNA polymerase are that it synthesizes DNA faster than the exonuclease in the reaction mixture degrades it. Suitable non strand-displacing DNA polymerases will be evident to the skilled worker. Among the preferred enzymes are the T7 gene 5 product, T4 DNA, polymerase, and *E. coli* PolI. Methods for preparing and using the above-noted DNA polymerases are conventional; and many are available commercially, e.g. from USB or NEB, as noted above.

Any DNA ligase can be used in the methods of the invention. The term "ligase" is sometimes used herein to refer to a DNA ligase. Suitable DNA ligases include, e.g., the T7 gene 1.3 product, T4 DNA ligase, *E. coli* DNA ligase and Taq Ligase. Methods for their preparation and optimal reaction conditions are conventional. Alternatively, they can be purchased from commercial sources, such as USB or NEB, as noted above. In a preferred embodiment, substantially all of the nicks (e.g., all of the nicks) are sealed during the reaction procedure, in order to prevent degradation by the exonuclease. However, in one embodiment, joined DNA which still comprises some nicks is transformed into a bacterium, such as *E. coli*, and the nicks are sealed by the bacterial machinery.

The four proteins used in the methods of the invention (the exonuclease, SSB, polymerase and ligase) may be contacted with the DNA molecules to be joined (e.g., added to a reaction mixture comprising a solution containing suitable salts, buffers, ATP, deoxynucleotides, etc. plus the DNA molecules) in any order. In one embodiment, the four proteins are added substantially simultaneously. For example, a mixture of the four proteins in suitable ratios can be added to the reaction mixture with a single pipetting operation. In other embodiments, the exonuclease is added last; and preceding the addition of the exonuclease, the SSB, polymerase and ligase are added sequentially, in any order, or two of the proteins are added substantially simultaneously, and the other protein is added before or after those two proteins. In one embodiment, the proteins are added in the following order: SSB, ligase, polymerase, exonuclease. A skilled worker can readily optimize the timing of the combination of the four individual proteins. In one embodiment, the four proteins are rapidly, sequentially added to the DNAs, within about 1-2 minutes of one another.

In another embodiment of the invention, the DNAs are added to a reaction mixture comprising a solution containing suitable salts, buffers, ATP, deoxynucleotides, etc. and the four proteins. In another embodiment, the DNAs are added to a reaction mixture comprising a solution containing suitable salts, buffers, ATP, deoxynucleotides, etc. and a subset of the four proteins, and the remaining proteins are then added, in any order or in any combination (e.g. the exonuclease is added last; and preceding the addition of the exonuclease, the SSB, polymerase and ligase are added sequentially, in any order, or two of the proteins are added substantially simultaneously, and the other protein is added before or after those two proteins).

In the methods of the invention, a plurality of DNA molecules are contacted with the four proteins under conditions "effective" to join the DNA molecules to form a substantially intact (preferably having no nicks) double stranded DNA molecule, in which a single copy of the region of sequence identity is retained. An important factor in achieving the joining is that the amount of 5' exonuclease activity should be substantially lower than the amount of DNA polymerase activity, so that the net assembly of DNA molecules is greater than the degradation of DNA molecules by the exonuclease. That is, the gaps formed by digestion by the 5' exonuclease are filled in by the polymerase substantially immediately after they are formed, and the intact (un-nicked) reaction product is "fixed" by the ligation reaction. Suitable amounts of activities include: exonuclease activity between about 0.1 and about 50 U/mL (unit defined by USB); DNA polymerase between about 10 and about 30 U/mL (unit defined by USB); SSB between about 0.1 and about 1 µM; and ligase between about 0.1 and about 1 µM. Lower amounts of polymerase would likely not able to catch up with the exonuclease, and higher amounts would likely degrade the 3' overhang generated by exonuclease, resulting in overlaps being digested before annealing can occur. Lower amounts of SSB would likely not allow annealing to occur rapidly enough, and higher amounts would likely stimulate exonuclease processivity, also resulting in polymerase cannot catch up. See Example I for some typical ratios that can be used.

Reaction conditions (such as the presence of salts, buffers, ATP, dNTPs, etc. and the times and temperature of incubation) are conventional and can be optimized readily by one of skill in the art. Preferably, the incubation temperature is about 25° C. to about 45° C., and the reaction is carried out for about 1-1.5 hours at 37° C., or for about 2-3 hours at 30° C. Typical reaction conditions are presented in Example I.

Because a non-strand displacing DNA polymerase used in the methods of the invention must elongate in the 5' direction from a primer molecule, the method cannot tolerate a free 5' end (e.g. at the 5' end of the most 5' DNA to be joined). Because no primer is available in such a molecule to be extended, such a molecule would be digested by the exonuclease and the resulting gap could not be filled in by a polymerase. In one embodiment, the 5' ends of the terminal DNA fragments that are joined are blocked so that 5' exonuclease cannot digest them. The blocking agent is preferably reversible, so that the joined DNA molecule can eventually be joined into a vector. Suitable blocking agents will be evident to the skilled worker. These include, e.g., phosphorothioate bonds, 5' spacer molecules, Locked Nucleic Acid (LNA) etc. In another embodiment of the invention, the fragments are selected (designed) so that the two terminal fragments join to one another to form a circle. In another embodiment, the joined fragments are designed so that they become integrated into a vector which is also present in the reaction mixture.

DNA molecules of any length can be joined by methods of the invention, and from two to an essentially unlimited upper level of DNA molecules can be joined. In general, at least about 10 fragments can be joined. The number of fragments which can be joined depends, e.g., on the length of the overlaps and the lengths of the fragments. For example, with fragments of greater than about 3 kb, having overhangs of about 150 to about 200 bp, the number of fragments that can be joined is substantially unlimited.

As noted above, in embodiments of the invention in which no blocker is used, the joined DNA molecules preferably form a circle and/or become ligated into a vector to form a circle. The lower size limit for a dsDNA to circularize is about 200 base pairs. Therefore, the total length of the joined fragments (including, in some cases, the length of the vector) is preferably at least about 200 by in length. There is no upper size limit, and joined DNAs of a few hundred kilobase pairs, or larger, can be generated by a method of the invention. Although the rate at which the circles can form may be reduced for very long molecules, that does not prevent the circle from forming and reaching a steady state in which the rate of filling in gaps is greater than the rate of exonuclease digestion, once all of the nicks have been sealed. Example I illustrates joining/recombination reactions in which four DNA molecules, of 2.2 kb, 1.5 kb, 1.55 kb and 1.2 kb, are joined.

In methods of the invention, the distal region of one of a pair of dsDNA molecules to be joined shares a region of sequence identity with the proximal region of the other dsDNA molecule. The term "distal" as used herein refers to the 3' end of a first DNA molecule of a pair to be joined (the 5'-most DNA molecule), and the term "proximal" refers to the 5' end of the second DNA molecule of the pair. The regions of identity are sometimes referred to herein as "overlaps" or "regions of overlap." FIG. 1 shows a schematic representation of the distal and proximal regions of DNA molecules to be joined. The region of sequence identity should be sufficiently long to allow the recombination to occur. The length can vary from a minimum of about 15 base pairs (bp) to a maximum of about 300 by or more. In general, it is preferable that the length of the overlap is not greater than about ⅒ the length of the fragment to be recombined; otherwise there may not be sufficient time for annealing and gap filling. For the joining of 2 or 3 fragments, about 20-30 by overlap may be sufficient. For more than 10 fragments, a preferred overlap is about 150 by to about 300 bp. If longer overlaps are used, the T7 endonuclease may also be required to debranch the joint molecules. In one embodiment, the region of sequence identity is of a length that allows it to be generated readily by synthetic methods, e.g. about 40 by (e.g., about 35 to about 45 bp).

In a preferred embodiment, when a plurality of DNA molecules are to be joined, for each pair of DNA molecules to be joined, the distal region of one of the DNA molecules of the pair is designed to share a region of sequence identity with the proximal region of the other DNA molecule of the pair, and the distal and proximal regions of sequence identity for each pair of DNA molecules are designed to be unique (to be different from the regions of sequence identity of the other pairs of DNA molecules). When the overlapping regions of identity are designed in this manner, the orientation and order of the DNA molecules in the joined molecule can be predetermined. A number of DNA molecules (for example, 4 or 6 molecules) can thus be incubated together in a single reaction mixture (in a single vessel or container) with the four proteins of the invention, and be joined into a longer DNA molecule in which the individual DNAs are arranged in any desired order and orientation.

The regions of sequence identity present in the proximal and distal regions of the DNAs to be joined can be generated by any of a variety of methods.

For example, in one embodiment of the invention, synthetically prepared fragments of a gene or genome of interest (e.g., about 5 kb in length) are optionally amplified (e.g. by PCR or by a rolling circle mechanism) and are joined by a method of the invention in the order and orientation in which they are located in the gene or genome. This procedure allows the preparation of a synthetic gene or genome. In this method, the first DNA fragment (e.g. in the 5' most portion of the gene or genome) is synthesized so that the region at its 3' end (the distal end) contains a sequence (e.g. about 40 bp) that is identical to the sequence at the 5' end (the proximal end) of the DNA fragment to which it is to be joined. The second DNA fragment, in turn, is synthesized so that it has, at its distal end, a sequence which is identical to the sequence at the proximal end of the third DNA fragment, and so on.

In other embodiments of the invention, the regions of identity are introduced by PCR amplification.

Figure 3:
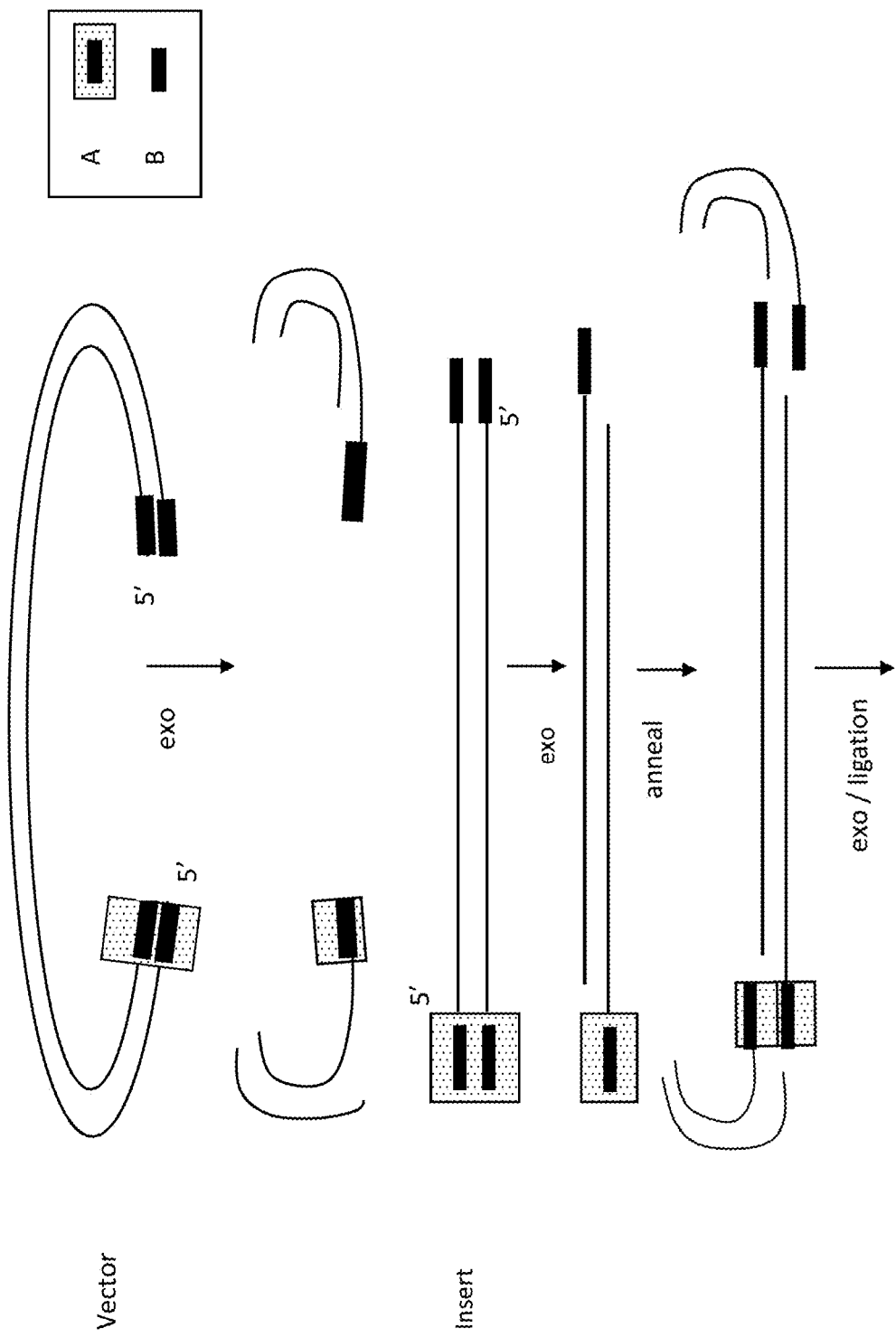
FIG. 3 is a cartoon illustrating a method for inserting a fragment into a vector.

In one such method, as illustrated in FIG. 3, a fragment of interest is inserted into a vector. For example, a plasmid vector can be linearized with a restriction enzyme, generating a sequence A (e.g. having 40 bp) to the left of the restriction enzyme cut and a sequence B (e.g. having 40 bp) to the right of the restriction enzyme cut. The fragment to be cloned into the vector is PCR amplified, using PCR primers which will introduce sequence A at the left end of the fragment, and sequence B at the right end of the fragment. The regions of sequence identity (in this example, each having 40 bp) allow the fragment to be joined to the vector in a desired orientation, to form a circular molecule. Alternatively, particularly when it is desirable to avoid errors which might be introduced into an insert during PCR amplification, the vector can be PCR amplified in order to introduce at the ends of a cloning site sequences which overlap sequences at the ends of the insert. This methods described above allow for the directional cloning of any insert of interest, without having to rely on the presence of, or introduction of, restriction enzyme sites on the insert.

Figure 2:
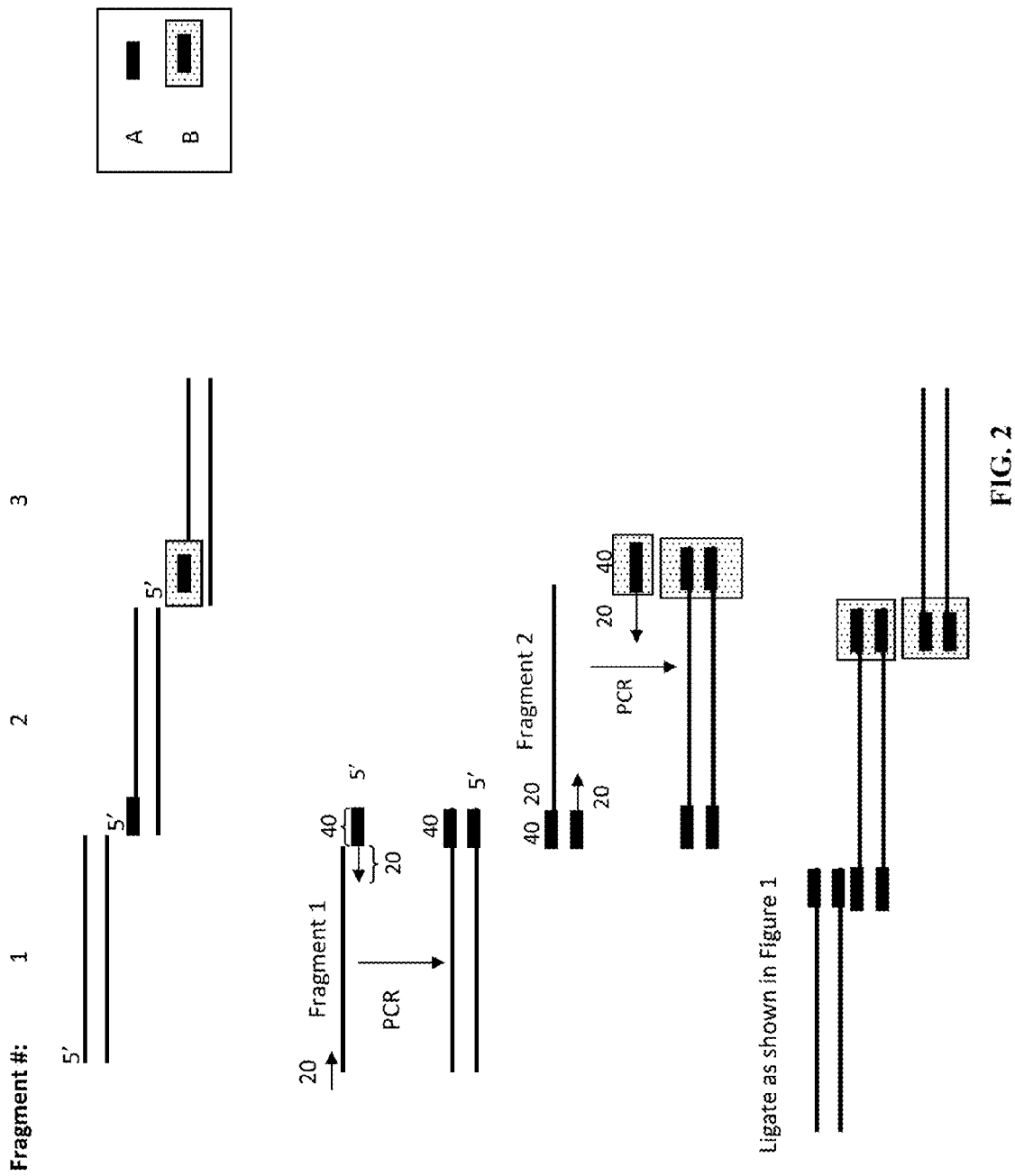
FIG. 2 is a cartoon illustrating a method for adding overlapping sequences by PCR amplification. As shown in the center panel, Fragment 1 is PCR amplified, to add sequence A at the 3' end. Fragment 2 is PCR amplified, to add sequence B to the 3' end. The joined molecules are shown as linear molecules; however, it is to be understood that the ends of the linear molecule are preferably joined to form a circle, and/or are joined to a linearized vector, to form a circle.
Figure 4:
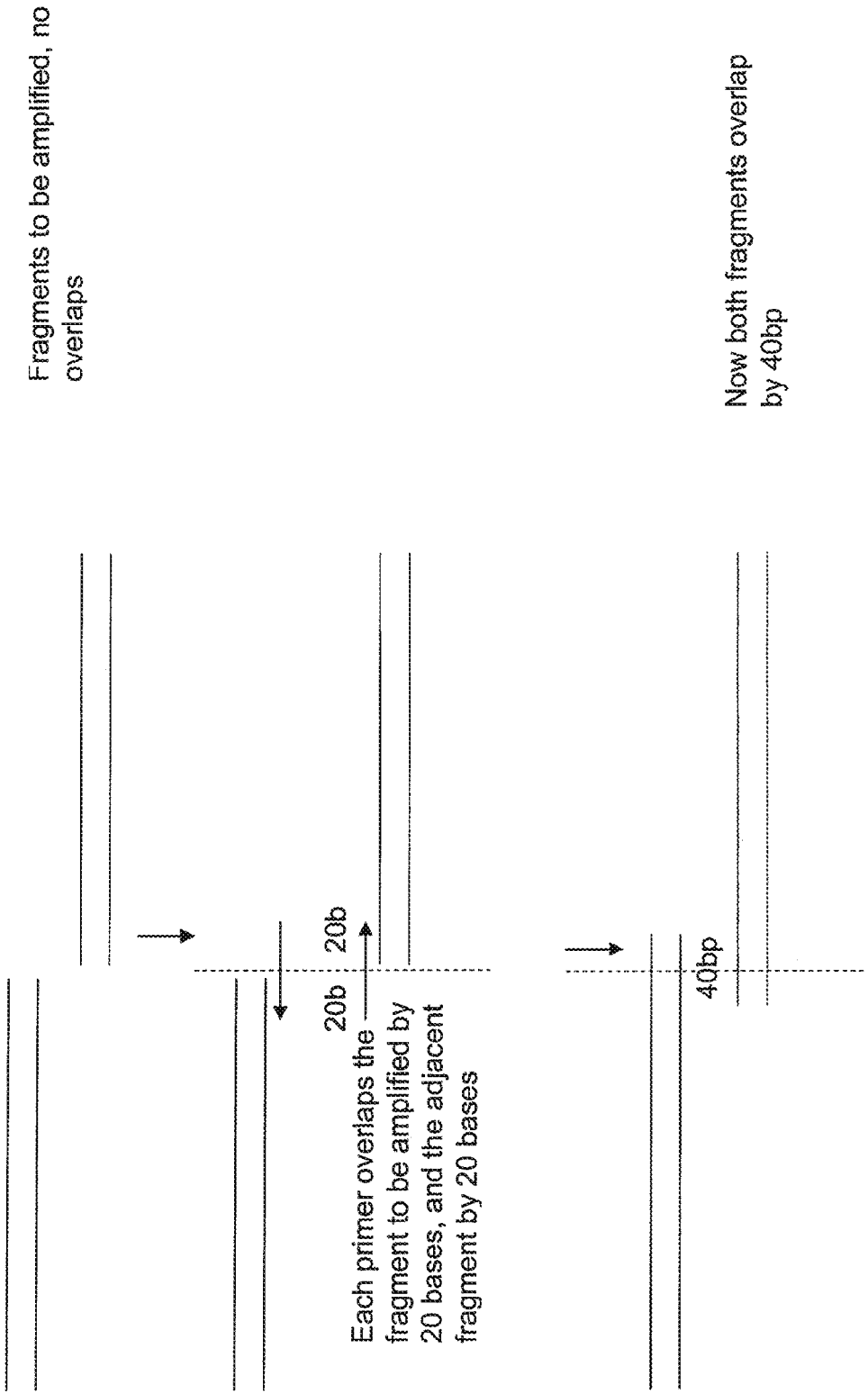
FIG. 4 is a cartoon illustrating a method for adding overlapping sequences by PCR amplification.

In another such method, as illustrated in FIG. 2, a plurality of DNA fragments are joined to one another. In this embodiment, the regions of sequence identity are introduced into the fragments by PCR amplification, using suitable primers. For each DNA fragment to be joined to another fragment, a sequence is introduced to the 3' (distal) end of the first fragment which overlaps with the sequence at the 5' (proximal) end of the fragment to which it is to be joined. PCR primers are used in which the regions of sequence identity (e.g. 40 nt) lie 5' to a PCR primer (e.g. having 20 nt). As shown in FIG. 2, after a suitable number of rounds of PCR amplification, DNA fragments are produced in which defined regions of sequence identity are present at the ends of the fragments. The resulting fragments can then be joined in a predetermined order and orientation by a method of the invention. A variant of this method is shown in FIG. 4. In this method, starting with two representative fragments having no regions of sequence identity at their ends, sequences are added by PCR amplification by primers having only 40 nt (instead of 60 nt); the resulting regions of sequence identity are 40 by in length. In FIGS. 1-3, the joined molecules are shown as linear molecules. As discussed above, the fragments at either end of a linear molecule are preferably joined to form a circle, and/or are joined to a linearized vector, to form a circle.

If desired, a vector can be present in the joining reaction, so that the joined fragments are introduced into the vector. The efficiency of joining a large number of fragments (e.g., 6 or 8 fragments) into a vector by a method of the invention is more efficient than when using a method which employs compatible restriction enzyme sites. To increase the efficiency even further, the DNAs from a joining reaction can be separated by size (e.g. by gel electrophoresis or a sizing column); and a DNA molecule of the desired size (having the correct number of joined fragments) can be isolated and introduced into a vector by a method of the invention.

In one embodiment, joined fragments and/or fragments inserted into vectors are introduced into a host cell, such as a bacterial or eukaryotic cell (e.g. by transfection or transformation). Alternatively, the reaction mixture comprising the joined DNA molecules can be introduced into a host cell; only those DNAs which have recombined to form circular molecules can survive in the host cell. In another embodiment, the joined fragments and/or fragments inserted into vectors are used directly, without further passage through a cell, such as a bacterial cell.

Molecular biology methods of the invention can be carried out using conventional procedures. See, e.g., discussions in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. (current edition) *Current Protocols in Human Genetics*, John Wiley & Sons, Inc.; and Coligan et al. (current edition) *Current Protocols in Protein Science*, John Wiley & Sons, Inc.

A variety of other uses for the inventive method will be evident to the skilled worker. In particular, the inventive method can be substituted for any method in which restriction enzyme digests are used to generate compatible sequences for joining DNA molecules. In one embodiment of the invention, DNA molecules that are too large to be amplified by PCR can be cloned by joining sub-fragments by a method of the invention and then inserting them into a suitable vector. An in vitro recombination system of the invention (e.g., the four proteins of the invention, in a suitable ratio) can be used to recombine any homologous DNAs of interest, e.g. to repair double stranded DNA breaks or gaps, etc. Another application of the method is to introduce a mutation into a DNA. In this method, a mutation is introduced into both the upper and lower strand PCR primers, so the amplified fragments are 100% mutant; then the fragments are joined by the method of the invention.

The disclosed methods can be used to join any nucleic acid molecules of interest. The nucleic acid molecules can come from any source, including a cellular or tissue nucleic acid sample, cloned fragments or subclones thereof, chemically synthesized nucleic acids, genomic nucleic acid samples, cDNAs, nucleic acid molecules obtained from nucleic acid libraries, etc. The DNAs can be radioactively labeled or can comprise binding entities, such a biotinylated nucleotides, which can aid in the purification of the joined DNAs. If desired, the DNA molecules to be joined, or primers for adding overlapping regions of sequence identity, can be prepared synthetically. Conventional synthesis techniques include using phosphoroamidite solid-phase chemistry to join nucleotides by phosphodiester linkages. Chemistry for joining nucleotides by phosphorothioate linkages or different linkages, such as methylphosphonate linkages, can also be used. For example, the cyanoethyl phosphoramidite method can be used, employing a Milligen or Beckman System 1 Plus DNA synthesizer (for example, Model 8700 automated synthesizer of Milligen-Biosearch, Burlington, Mass. or ABI Model 380B). Synthetic methods useful for making DNA molecules are also described by Ikuta et al. (1984) *Ann Rev. Biochem.* 53, 323-356, (phosphotriester and phosphite-triester methods), and Narang et al. (1980) *Methods Enzymol.* 65, 610-620 (phosphotriester method). DNAs prepared by methods as above are available from commercial sources, such as Integrated DNA Technologies (IDT), Coralville, Iowa.

Methods of the invention can be carried out in a high throughput fashion, using automated (e.g. robotic) systems, which allow many DNA joining reactions to be carried out simultaneously.

Any combination of the materials useful in the disclosed methods can be packaged together as a kit for performing any of the disclosed methods. For example, the four proteins: a non-processive 5' exonuclease (e.g., the phage T7 gene 6 product); a single stranded DNA binding protein (SSB) which accelerates nucleic acid annealing (e.g., the T7 gene 2.5 product or the *E. coli* recA protein); a non strand-displacing DNA polymerase (e.g., the T7 gene 5 product, T4 DNA polymerase, and *E. coli* pol I); and a ligase (e.g., T4 DNA ligase or *E. coli* DNA ligase) can be packaged individually or in various combinations. In one embodiment, the four proteins are packaged together in a single container (such as an Eppendorf tube). In another embodiment, the exonuclease is packaged separately, so that this enzyme can be added last to a reaction mixture containing the DNA molecules to be joined and the other three proteins. In a preferred embodiment, the SSB, polymerase and ligase are packaged together in suitable ratios so that an aliquot can be removed and added to a reaction mixture containing DNAs so that, following the addition of an exonuclease, DNA joining takes place. If desired, the protein reagents can be packaged in single use form, suitable for carrying one set of DNA joining reactions.

Optionally, kits of the invention comprise instructions for performing the method. Other optional elements of a kit of the invention include suitable buffers, packaging materials, etc. The protein reagents of the kit may be in containers in which they are stable, e.g., in lyophilized form or as stabilized liquids. Preferably, the proteins are stored as solutions in 50% glycerol.

DNAs used in methods of the invention can have one or more modified nucleotides. For example, they may contain one or more modifications to either the base, sugar, or phosphate moieties. Modifications to the base moiety would include natural and synthetic modifications of A, C, G, and T as well as different purine or pyrimidine bases, such as uracil-5-yl, hypoxanthin-9-yl (1), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al. (1991) *Angewandte Chemie, International Edition* 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)nO]mCH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON [(CH$_2$)nCH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$, CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3-alkylene phosphonate and chiral phosphonates, phosphinates, phosphoramidates including 3'-amino phosphoramidate and aminoalkylphosphoramidates, thionophosphoramidates, thionoalkyl¬phosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

It is understood that nucleotide analogs need only contain a single modification, but may also contain multiple modifications within one of the moieties or between different moieties.

Nucleotide substitutes are nucleotides or nucleotide analogs that have had the phosphate moiety and/or sugar moieties replaced. Nucleotide substitutes include molecules having similar functional properties to nucleotides, but which do not contain a phosphate moiety, such as peptide nucleic acid (PNA). Nucleotide substitutes include molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate back-bones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules. See also Nielsen et al. (1991) Science 254, 1497-1500.

DNA molecules of the invention can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

In the foregoing and in the following example, all temperatures are set forth in uncorrected degrees Celsius; and, unless otherwise indicated, all parts and percentages are by weight.

EXAMPLES

Example I

Figure 5:
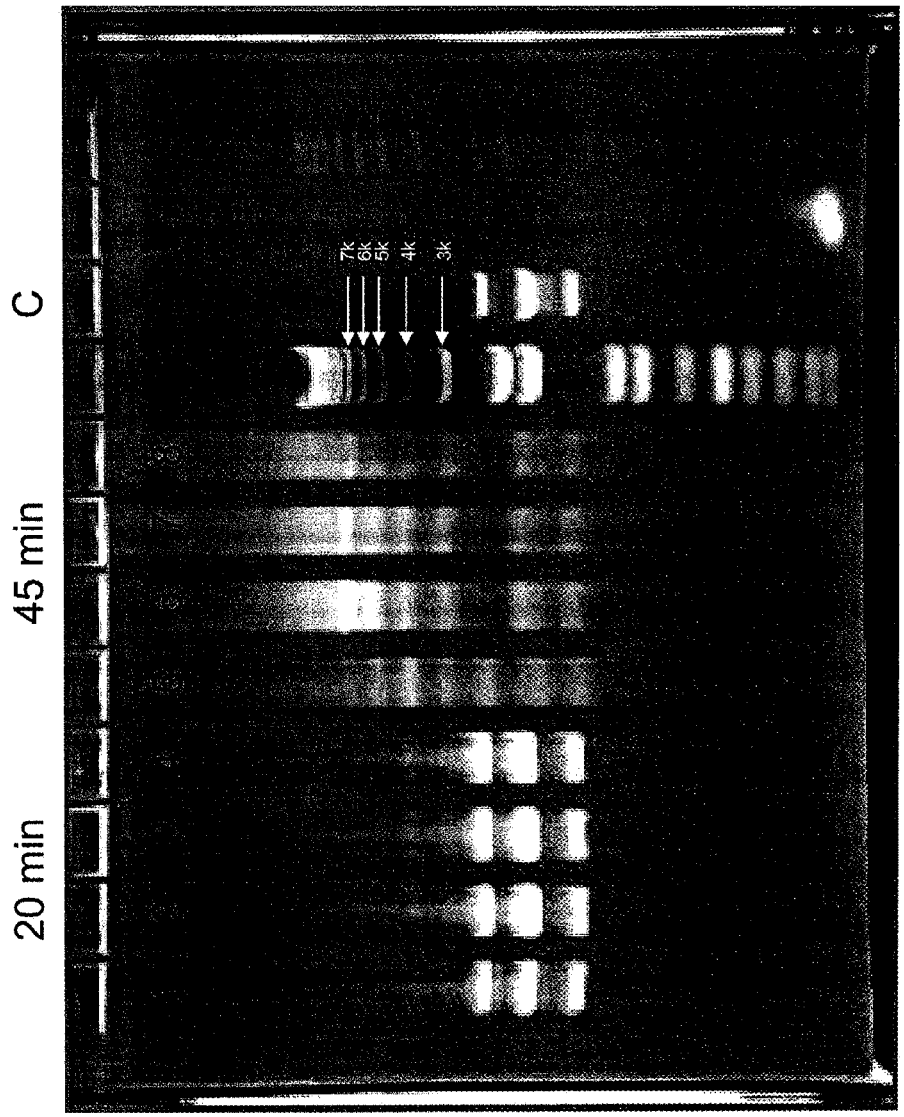
FIG. 5 shows the results of incubating four DNA fragments by a method of the invention, for 20 minutes or 45 minutes. Lanes 1-4 show results from incubation for 20 min, lanes 5-8 show results from incubation for 45 min at 30° C. The reaction for each lane started with 6 µg total DNA (4 fragments of 2.2 kb, 1.5 kb, 1.55 kb and 1.2 kb), 30 U/ml T7 DNA polymerase, and 4000 U/ml T4 DNA ligase. Lanes 1-4 and 5-8 show results from reactions containing 20, 2, 4, 0.4 U/ml exonuclease and 1, 1.5, 2, 2 µM T7 ssb, respectively.
Figure 6:
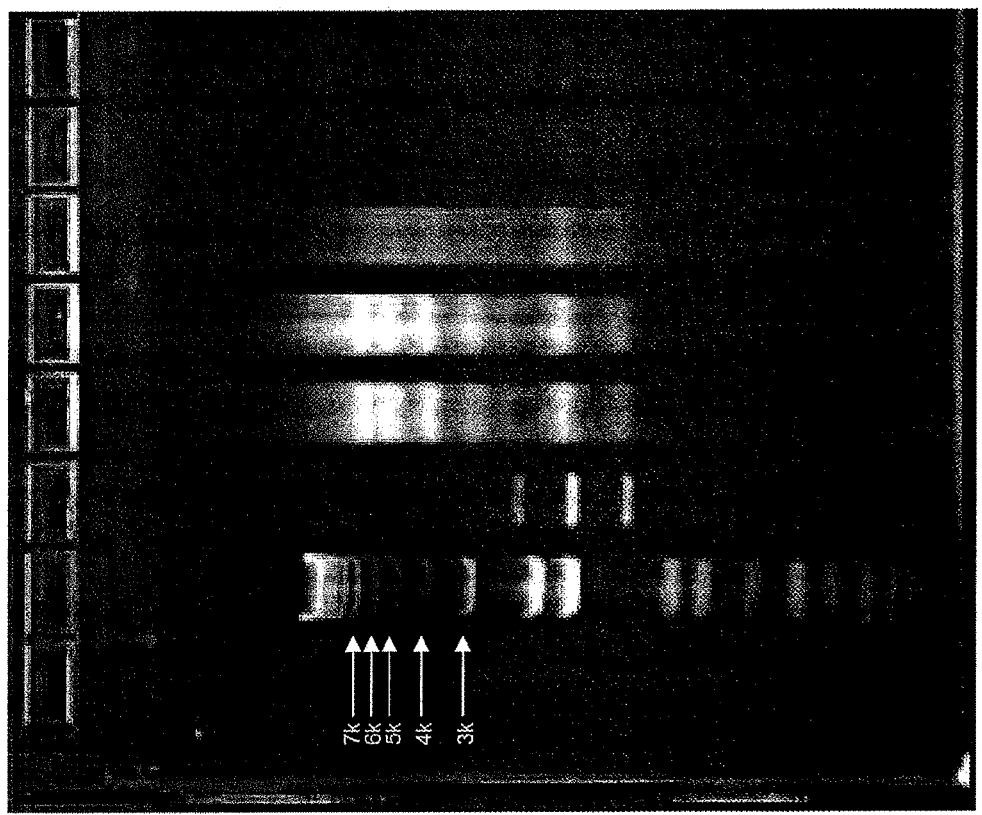
FIG. 6 shows the results of incubating four DNA fragments by a method of the invention, for 60 minutes. Conditions were similar to those for lane 2 and 6 of FIG. 5. Lane 1 shows results of a reaction with control DNA only. Lanes 2 and 3 show results from duplicates, incubated at 30° C. for 60 minutes. Lane 4 shows results of a sample without ligase. Lane 5 shows results from a sample without ssb.

Four DNA molecules, having lengths of 2.2 kb, 1.5 kb, 1.55 kb and 1.2 kb, were incubated according to a method of the invention, under the conditions noted in FIGS. 5 and 6. The reaction mixes were subjected to gel electrophoresis, along with molecular weight markers. When the samples were incubated for 45 minutes or 60 minutes, a major band of about 6.3 kb formed. This is the size expected for a joined product containing one copy of each of the DNAs.

Example II 4 enzymes (T7 5'-exonuclease, Taq polymerase, VENT polymerase, and Taq ligase) plus two or more overlapping DNA fragments which can form a circular DNA molecule when recombined, are recombined in a single reaction mixture such that the final product is a circular molecule containing the recombined fragments.

T7 5'-exonuclease is used to chew-back the 5'-ends of the duplex DNA fragments, thus exposing the overlapping regions. This enzyme has no activity on 3'-ends. It acts at free ends and at nicks in the DNA. Once the overlaps are exposed, they can anneal to form joints that can be repaired because the 3'-ends of the annealed regions can be extended by the Taq polymerase, which prior to the exposure and annealing of the overlaps was inactive in the reaction mixture. The purpose of the VENT polymerase, which is in very low amount, is to remove any single 3' nucleotide additions that are produced by the Taq polymerase on the DNA fragments ends prior to the action of the T7 exonuclease. When the extending 3' ends catch up to the 5'-ends, the Taq ligase completes the repair by ligating the 5'-3' nick. The repaired joint is then resistant to further reaction by the enzymes. When the fragments are joined into a complete circle, that product is resistant to further reaction and is the desired end product of the reaction.

Annealing of the overlapping ends is accelerated by carrying out the reaction at elevated temperature (e.g. 45 to 60° C.) in the presence of 5% PEG 8000 in the reaction buffer.

For an efficient reaction the enzymes must be balanced in amount so that the T7 degradation is somewhat slower than the rate of annealing, polymerization, and ligation. Taq ligase should be in large excess so that repair is completed as soon as the polymerization fills in the gaps created when the overlapping ends anneal with each other.

A suitable buffer for the reaction contains 20 mM Tris acetate, 50 mM potassium acetate, 10 mM magnesium chloride, 5 mM DTT, 25 ug per ml BSA, 5% PEG-8000, 200 uM dNTP's, 1 mM NAD, 0.1% Triton X-100, adjusted to pH 7.9.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications cited above and in the figures are hereby incorporated by reference.

The invention claimed is:

1. A kit for in vitro joining a plurality of dsDNA molecules, consisting essentially of in a single container,
   a mixture of the isolated proteins
   (i) a single stranded DNA binding protein (SSB) which accelerates nucleic acid annealing,
   (ii) a non strand-displacing DNA polymerase, and
   (iii) a ligase;
   (iv) an isolated non-processive 5' exonuclease; and
   (v) glycerol in an amount effective as a preservative;
   wherein the ratios of activities of (i), (ii), (iii), and (iv) are effective to achieve in vitro joining of dsDNA molecules, and
   wherein the dsDNA molecules are joined via a region of sequence homology to form a DNA molecule in which a single copy of the region of sequence homology is retained.

2. The kit of claim 1, wherein the mixture contains
   (i) as the SSB, the phage T7 gene 2.5 product, the *E. coli* recA protein, RedB of lambda phage, or RecT of Rae prophage;
   (ii) as the DNA polymerase, the T7 gene 5 product, T4 polymerase, or *E. coli* pol; and/or
   (iii) as the ligase, the phage T7 gene 1.3 product, phage T4 DNA ligase, or *E. coli* DNA ligase; and/or
   (iv) as the 5' exonuclease, the phage T7 gene 6 product, RedA of lambda phage, or RecE of Rae prophage.

3. The kit of claim 2 wherein:
   (i) the phage T7 gene 2.5 product, the *E. coli* recA protein, RedB of lambda phage, or RecT of Rae prophage are substantially purified;
   (ii) the T7 gene 5 product, T4 polymerase, or *E. coli* pol are substantially purified; and/or
   (iii) the phage T7 gene 1.3 product, phage T4 DNA ligase, or *E. coli* DNA ligase are substantially purified.

4. The kit of claim 3 wherein the non-processive 5' exonuclease is substantially purified.

5. The kit of claim 3 further comprising instructions for performing a method for the in vitro joining of a plurality of dsDNA molecules.

6. The kit of claim 1 wherein:
   (i) the single stranded DNA binding protein (SSB) is substantially purified;
   (ii) the non strand-displacing DNA polymerase is substantially purified, and
   (iii) the ligase is substantially purified.

7. The kit of claim 6 wherein the non-processive 5' exonuclease is substantially purified.

8. The kit of claim 6 further comprising instructions for performing a method for the in vitro joining of a plurality of dsDNA molecules.

9. A composition consisting essentially of:
   (a) a substantially purified single stranded DNA binding protein (SSB) which accelerates nucleic acid annealing,
   (b) a substantially purified non strand-displacing DNA polymerase,
   (c) a substantially purified ligase, and
   (d) substantially purified non-processive 5' exonuclease, and
   (e) glycerol in an amount effective as a preservative;
   wherein the ratios of activities of (a), (b), (c) and (d) are effective to achieve in vitro joining of dsDNA molecules via a region of homology.

* * * * *